(12) United States Patent
Yamaki

(10) Patent No.: US 8,273,336 B2
(45) Date of Patent: Sep. 25, 2012

(54) HAIR TREATMENT COMPOSITION

(75) Inventor: Satoshi Yamaki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/255,049

(22) PCT Filed: Mar. 5, 2010

(86) PCT No.: PCT/JP2010/053678
§ 371 (c)(1),
(2), (4) Date: Oct. 5, 2011

(87) PCT Pub. No.: WO2010/101253
PCT Pub. Date: Sep. 10, 2010

(65) Prior Publication Data
US 2012/0052032 A1    Mar. 1, 2012

(30) Foreign Application Priority Data

Mar. 6, 2009 (JP) .................... 2009-054019

(51) Int. Cl.
*A61K 8/41* (2006.01)
(52) U.S. Cl. .................. 424/70.21; 424/28
(58) Field of Classification Search ........... 424/70.21, 424/70.28
See application file for complete search history.

(56) References Cited

U.S. PATENT DOCUMENTS

| | | | |
|---|---|---|---|
| 2005/0013789 A1* | 1/2005 | Sakai et al. | 424/70.21 |
| 2005/0142091 A1* | 6/2005 | Watanabe | 424/70.12 |
| 2006/0233734 A1* | 10/2006 | Inoue et al. | 424/70.21 |
| 2007/0071709 A1* | 3/2007 | Tokunaga | 424/70.28 |
| 2008/0050330 A1* | 2/2008 | Ishino | 424/70.12 |

FOREIGN PATENT DOCUMENTS

| | | |
|---|---|---|
| JP | 10-182362 | 7/1998 |
| JP | 10-330619 | 12/1998 |
| JP | 2003-081780 | 3/2003 |
| JP | 2003-081783 | 3/2003 |
| JP | 2003-176212 | 6/2003 |
| JP | 2004-002261 | 1/2004 |
| JP | 2004-508313 | 3/2004 |
| JP | 2005-298447 | 10/2005 |
| JP | 2005-306786 | 11/2005 |

(Continued)

OTHER PUBLICATIONS

STIC Search Report dated Jun. 6, 2012.*

(Continued)

*Primary Examiner* — Eisa Elhilo
(74) *Attorney, Agent, or Firm* — Andrew F. Young, Esq.; Lackenbach Siegel, LLP

(57) ABSTRACT

Disclosed is a pretreatment agent which can achieve a chemical treatment such as the formation of permanent waves or hair-dye uniformly only by pre-treating hair with the pretreatment agent, and which can impart smooth and soft touch to hair as if a hair treatment is applied to the hair after the chemical treatment. Specifically disclosed is a hair treatment composition which is characterized by comprising (A) a tertiary amine, (B) a quaternary ammonium salt and (C) a higher alcohol, wherein the ratio of the content of the higher alcohol to the total content of the tertiary amine and the quaternary ammonium salt is 0.1 to 1.0 by weight and the pH value of the whole composition is 7.0 or higher.

11 Claims, 2 Drawing Sheets

FOREIGN PATENT DOCUMENTS

| | | |
|---|---|---|
| JP | 2005-343860 | 12/2005 |
| JP | 2006-290795 | 10/2006 |
| JP | 2007-161605 | 6/2007 |
| JP | 2007-262046 | 10/2007 |
| JP | 2008-513509 | 5/2008 |
| JP | 2008-127337 | 6/2008 |
| JP | 2009-126850 | 6/2009 |
| WO | WO 2010/101253 | 9/2010 |

OTHER PUBLICATIONS

Japanese Office Search Report for PCT/JP2010/053678 filed Mar. 5, 2010, (both JP and English 6 pages).

* cited by examiner

[FIG. 1]
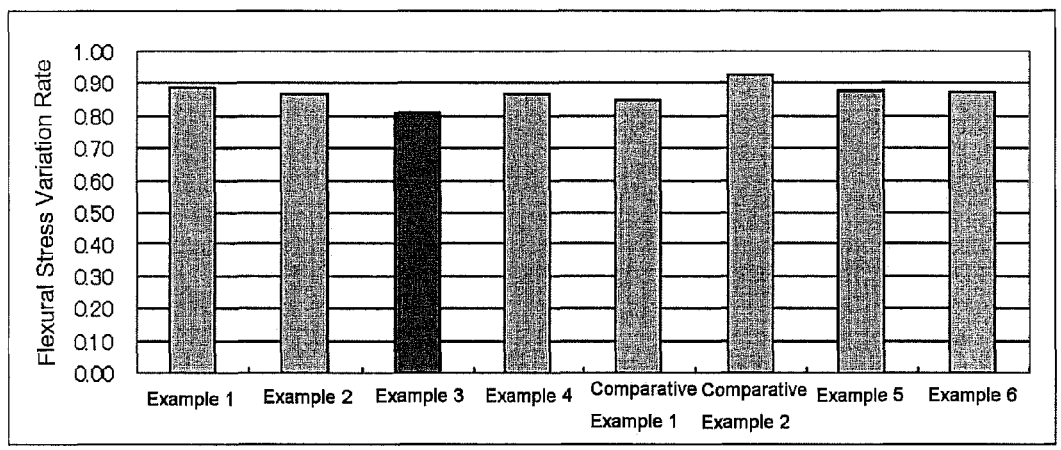
[FIG. 2]
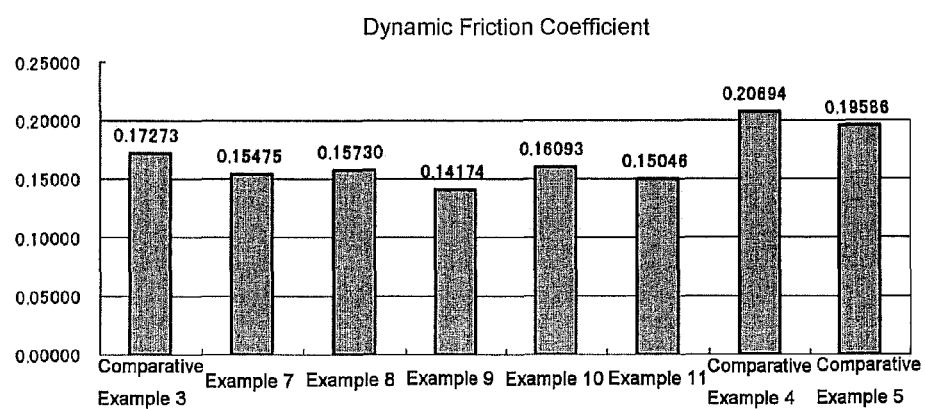

[FIG. 3]
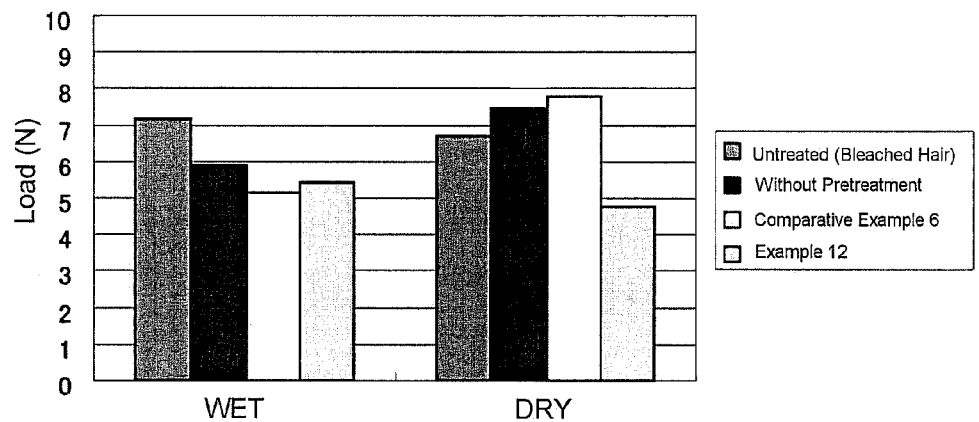
[FIG. 4]
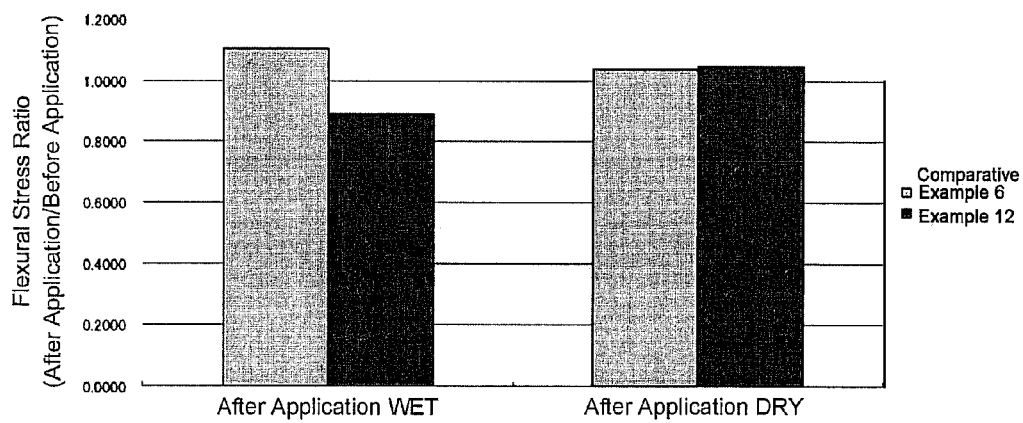

HAIR TREATMENT COMPOSITION

CROSS REFERENCE TO RELATED APPLICATIONS

This application relates to and claims priority from PCT/JP2010/053678 filed Mar. 5, 2010, the entire contents of which are incorporated herein by reference, which in turn claims priority from JP 2009-054019 filed Mar. 6, 2009.

FIGURE SELECTED FOR PUBLICATION

FIG. 3

BACKGROUND OF THE INVENTION

1. Field of the Invention

The present invention relates to a hair treatment composition. More specifically, the present invention relates to a hair treatment composition which is applied to the hair mainly before performing a chemical treatment such as permanent wave formation or dyeing and is capable of imparting an excellent touch to the hair after the chemical treatment.

2. Description of the Related Art

A chemical treatment (chemical procedure) on the hair, such as permanent wave formation, dyeing, and/or bleaching is generally performed as a treatment of performing an aesthetic treatment in terms of a shape or a color on the hair. However, a chemical reagent such as an acid, an alkali, an oxidant, a reducing agent, and a dye compound is used in the chemical treatment, and the chemical reagent is known to damage the hair.

It has been an ordinary practice to restore smoothness of the hair or to condition a surface state of the hair by performing a hair treatment using a conditioner on the hair which is damaged by the chemical treatment. For the hair treatments, a treatment agent containing a cationic surfactant of which a typical example is alkyl trimethyl ammonium chloride, oil, a moisturizing agent, and the like is used (see Patent Document 1, for example). Also, a composition intended for use for omitting a post-treatment step, which is obtained by blending an active ingredient with a dyeing or bleaching agent, has been proposed (Patent Document 2).

On the other hand, in the chemical treatment such as the permanent wave formation and the dyeing, it has been known that effect is varied depending on the absence/presence of a damage of the hair to be treated, and, in the case where the hair having a partial damage is subjected to the chemical treatment, a color or wave formation is varied depending on a portion to often cause color unevenness or shape non-uniformity.

In order to solve the above-described problems, a pretreatment agent for repairing a damage of the hair before performing the chemical treatment has been used. For example, a pretreatment agent for permanent wave treatment, containing an oxidation decomposition product of keratin having a predetermined molecular weight is described in Patent Document 3, and a pretreatment agent for hair coloring, containing a cationized cellulose and a cationic surfactant is described in Patent Document 4.

RELATED ART DOCUMENTS

Patent Document 1: JP A Hei 5-43438
Patent Document 2: JP A Hei 11-193223
Patent Document 3: JP A 2003-40742
Patent Document 4: JP A 2006-282512

ASPECTS AND SUMMARY OF THE INVENTION

Problem to be Solved by the Invention

However, although a certain degree of effect is confirmed in terms of repair of a damage of the hair and attainment of permanent wave formation or dyeing by the use of the conventional pretreatment agents, the conventional pretreatment agents are not capable of imparting an excellent hair texture as if a hair treatment was performed to the hair after the chemical treatment and requires a treatment after the chemical treatment.

Accordingly, an object of the present invention is to provide a pretreatment agent which enables to uniformly perform a chemical treatment such as permanent wave formation and dyeing only by performing a pretreatment on the hair and further to attain a smooth and soft hair texture as if a hair treatment is performed after the chemical treatment.

Means for Solving Problem

The inventors had conducted extensive research to solve the above-described problems to find that it is possible to impart an excellent texture to the hair after a chemical treatment by performing a pretreatment using a hair treatment composition obtainable by blending a tertiary amine, a quaternary ammonium salt, and a higher alcohol at a predetermined ratio and adjusting a pH to 7.0 or more, thereby accomplishing the present invention.

Accordingly, the present invention provides a hair treatment composition including: (A) a tertiary amine represented by the following formula (I):

(wherein R1 may be the same or different and each represents a C1-3 alkyl group or benzyl group which may optionally be substituted by a hydroxyl group; and R2 represents a C8-36 straight chain or branched chain alkyl group which may optionally be substituted by a hydroxyl group or a R3—(Y)—(Z)-group, in which R3 is a C8-36 straight chain or branched chain alkyl group which may optionally be substituted by a hydroxyl group; Y is a linking group selected from an amide linkage (—CONH—), an ether linkage (—O—), and an ester linkage (—COO—); and Z is a linking group selected from —CH2CH2CH2— and —CH2CH(OH)CH2—);

(B) a quaternary ammonium salt represented by the following formula (II):

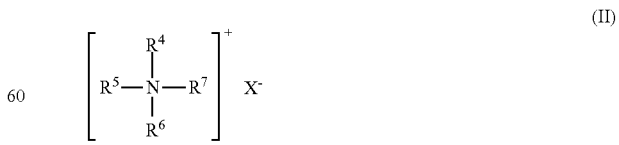

(wherein R4, R5, R6, and R7 may be the same or different with at least one of R4, R5, R6, and R7 representing a C3-36 straight chain or branched chain alkyl group or alkenyl group while each of the rest representing a C1-3 alkyl group or benzyl group which may optionally be substituted by a hydroxyl group; and X— represents an anion); and (C) a higher alcohol, characterized in that a ratio ((C)/[(A)+(B)]) of an amount of the higher alcohol (C) to a total amount ([(A)+(B)]) of the tertiary amine (A) and the quaternary ammonium salt (B) is within a range of 0.1 to 1.0; and that the composition as a whole has a pH of 7.0 or more.

Effect of the Invention

Even after performing a chemical treatment such as a permanent wave formation, dyeing, or the like, a pretreatment with a hair treatment composition of the present invention enables to attain an excellent hair texture which is equal to or better than the case of performing a hair treatment after the chemical treatment.

Also, since the hair treatment composition of the present invention is a single composition, and since it is possible to apply a permanent wave agent or a dyeing agent without washing off the hair treatment composition, usability thereof is considerably excellent.

The above, and other aspects, features and advantages of the present invention will become apparent from the following description read in conjunction with the accompanying drawings, in which like reference numerals designate the same elements.

BRIEF DESCRIPTION OF THE DRAWINGS

FIG. 1 is a graph showing results of measurements each of which was conducted for measuring flexibility (softness) of the hair in terms of a flexural stress variation rate of the hair before and after a treatment with each of compositions of Examples 1 to 6 and Comparative Examples 1 and 2.

FIG. 2 is a graph showing results of measurements each of which was conducted for measuring smoothness of the hair in terms of a dynamic friction coefficient of the hair before and after a treatment with each of compositions of Examples 7 to 11 and Comparative Examples 3 to 5.

FIG. 3 is a graph showing results of combing tests each of which was conducted for measuring smoothness of the hair after oxidation dyeing of the hair on which the composition of Example 12 or Comparative Example 6 was applied.

FIG. 4 is a graph showing results of measurements each of which was conducted for measuring flexibility (softness) of the hair in terms of a flexural stress variation of the hair after oxidation dyeing of the hair on which the composition of Example 12 or Comparative Example 6 was applied.

DETAILED DESCRIPTION OF THE PREFERRED EMBODIMENTS

Reference will now be made in detail to embodiments of the invention that are illustrated in the discussion herein.

MODES FOR CARRYING OUT THE INVENTION

A tertiary amine (A) forming the hair treatment composition of the present invention is one or a mixture of two or more selected from tertiary amines represented by the following formula (I):

(wherein $R^1$ may be the same or different and each represents a $C_{1-3}$ alkyl group or benzyl group which may optionally be substituted by a hydroxyl group; and $R^2$ represents a $C_{8-36}$ straight chain or branched chain alkyl group which may optionally be substituted by a hydroxyl group or a $R^3$—(Y)—(Z)-group, in which $R^3$ is a $C_{8-36}$ straight chain or branched chain alkyl group which may optionally be substituted by a hydroxyl group; Y is a linking group selected from an amide linkage (—CONH—), an ether linkage (—O—), and an ester linkage (—COO—); and Z is a linking group selected from —$CH_2CH_2CH_2$— and —$CH_2CH(OH)CH_2$—).

Specific examples of the tertiary amine represented by the formula (I) includes behenyl methylamine, stearyldimethylamine, dimethylaminopropylamide stearate, diethylaminopropylamide stearate, stearoxypropyl dimethylamide, N-(2-hydroxy-3-stearoxypropyl)-N,N-dimethylamine, behenamidopropyl dimethylamine, stearamidopropyl methanolamine, stearoxypropyl dimethylamine, and the like.

An amount of the tertiary amine to be contained in the hair treatment composition of the present invention may ordinarily be 0.01 to 10% by mass, preferably 1 to 5% by mass. It is difficult to attain a satisfactory hair treatment effect when the amount is less than 0.01% by mass, while no further improvement in property is attained when the amount exceeds 10% by mass.

The quaternary ammonium salt (B) forming the hair treatment composition of the present invention is one or a mixture of two or more selected from quaternary ammonium salts represented by the following formula (II):

(wherein $R^4$, $R^5$, $R^6$, and $R^7$ may be the same or different with at least one of $R^4$, $R^5$, $R^6$, and $R^7$ representing a $C_{3-36}$ straight chain or branched chain alkyl group or alkenyl group while each of the rest representing a $C_{1-3}$ alkyl group or benzyl group which may optionally be substituted by a hydroxyl group; and $X^-$ represents an anion). Particularly, the quaternary ammonium salt having the $C_{12-18}$ alkyl group or alkenyl group is preferred since it has an effect of imparting high flexibility to the hair.

The counter anion ($X^-$) in the formula (II) is not particularly limited insofar as it is capable of forming a salt with a quaternary ammonium. Examples of the anion include a halogen atom, a $C_{1-2}$ alkyl sulfuric acid, an organic acid, and the like.

Specific examples of the quaternary ammonium salt represented by the formula (II) include lauryltrimethylammonium chloride, lauryltrimethylammonium bromide, myristyltrimethylammonium chloride, myristyltrimethylammonium bromide, cetyltrimethylammonium chloride, cetyltrimethylammonium bromide, stearyltrimethylammonium chloride, stearyltrimethylammonium bromide, behenyltrimethylammonium chloride, behenyltrimethylammonium bromide, cetyltrimethylammonium methanesulfonate stearyltrimethylammonium metho sulfate, myristyldimethylbenzyl ammonium chloride, cetyldimethylbenzylammonium chloride, stearyldimethyl dimethylbenzylammonium chloride, octyldihydroxyethylmethylammonium chloride, 2-decyltetradecyltrimethylammonium chloride, 2-dodecylhexadecyltrimethyl ammonium chloride, distearyldimethylammonium chloride, dicetyldimethylammonium chloride, dicocoyldimethylammonium chloride, and the like.

An amount of the quaternary ammonium salt to be contained in the hair treatment composition of the present invention may ordinarily be 0.01 to 10% by mass, preferably 0.1 to 5% by mass. It is difficult to attain a satisfactory hair treatment effect when the amount is less than 0.01% by mass, while no further improvement in property is attained when the amount exceeds 10% by mass.

As the higher alcohol (C) forming the hair treatment composition of the present invention, those ordinarily used for cosmetics, medicines, and the like are usable. Among others, a straight chain alcohol having 16 or more carbon atoms is preferred since it enables the composition to maintain an appropriate viscosity and attains good use feeling and stability of a product. Particularly, a $C_{16-22}$ straight chain alcohol such as stearyl alcohol, behenyl alcohol, oleyl alcohol, cetostearyl alcohol, and the like is preferred.

Examples of the higher alcohol include a straight chain alcohol (e.g. lauryl alcohol, cetyl alcohol, stearyl alcohol, behenyl alcohol, myristyl alcohol, oleyl alcohol, cetostearyl alcohol, hardened rapeseed oil alcohol, etc.), a branched chain alcohol (e.g. monostearyl glycerin ether (batyl alcohol), 2-decyl tetradecinol, lanoline alcohol, cholesterol, phytosterol, hexyldodecanol, isostearyl alcohol, octyl dodecanol, etc.), and the like.

An amount of the higher alcohol to be contained in the hair treatment composition of the present invention may ordinarily be 0.01 to 10% by mass, preferably 0.1 to 5% by mass. It is difficult to attain a satisfactory hair treatment effect when the amount is less than 0.01% by mass, while no further improvement in property is attained when the amount exceeds 10% by mass.

In the hair treatment composition of the present invention, a ratio ((C)/[(A)+(B)]) of the amount (weight) of the higher alcohol (C) to a total weight ([(A)+(B)]) of the amounts of the tertiary amine (A) and the quaternary ammonium salt (B) is ordinarily adjusted to be within a range of from 0.1 to 1.0, preferably from 0.2 to 0.8. An unfavorable state in terms of stability, such as separation of the product, is caused when the ratio is less than 0.1, while the properties of the product regarding smoothening and softening hair tend to be deteriorated when the ratio exceeds 1.0.

Further, a pH of the hair treatment composition of the present invention is ordinarily be adjusted to 7.0 or more, preferably 7.2 or more, more preferably 7.5 or more. The desired effect of the present invention is not attained when the pH is lowered to less than 7.0 to be acidic. An upper limit of the pH is not particularly limited but may ordinarily be about 9 or less, preferably about 8.5 or less.

Adjustment of the pH of the composition may be attained by adding an acidifying agent or a basifying agent. In general, a base obtained by mixing the tertiary amine and the quaternary ammonium in the above-specified amount shows a pH value near 9, it is possible to neutralize the base by appropriately adding an acid such as glutamic acid, lactic acid, citric acid, malic acid, tartaric acid, hydrochloric acid, phosphoric acid, and the like.

Characteristics of the present invention with the above-specified mixing ratio and pH are in contrast to the conventional hair treatment agents (agent which is applied to the hair after chemical treatment) which generally contain a small amount of a cationic surfactant and a large amount of a higher alcohol and are acidic compositions, and it has been impossible to anticipate from the conventional art that the hair treatment composition of the present invention having such characteristics can exhibit the excellent treatment effect.

The hair treatment composition of the present invention may contain other arbitrary components which are ordinarily contained in a hair treatment agent such as a conditioner within a range which satisfies the above-described conditions.

Examples of the other arbitrary components include hydrocarbon oil other than the higher alcohol, oil such as silicone oil, a moisturizing agent, an ionic polymer, a nonionic polymer, an ionic surfactant, a nonionic surfactant, a preservative, a coloring agent, and the like.

The hair treatment composition of the present invention may be in various formulations, but an oil-in-water emulsion is preferred from the viewpoint of usability. It is possible to prepare the hair treatment composition in the form of an emulsion by, for example, adding the tertiary amine, the quaternary ammonium salt, the higher alcohol, and the other arbitrary components to water which is heated to about 80° C., dissolving the components by stirring, performing an emulsifying processing by using a homomixer, for example, and cooling. It is possible to prepare the compositions in other formulations by techniques which are generally used for production of cosmetics.

The hair treatment composition of the present invention may preferably be used as a pretreatment agent which is used before a chemical treatment but may be used simultaneously with the chemical treatment.

EXAMPLES

Hereinafter, the present invention will be described in more details by using specific example, but the scope of the present invention is not limited to the specific examples. An amount in the present specification means % by mass unless otherwise noted.

Examples 1 to 6 and Comparative Examples 1 and 2

Hair treatment compositions containing the components listed in Table 1 shown below were prepared.

Production process: Each of the compositions was obtained by adding other components to hot water of 80° C., dissolving by stirring, and cooling to 40° C. A change in flexibility (softness) of the hair before and after application of each of the compositions was measured.

TABLE 1

|  | Example 1 | Example 2 | Example 3 | Example 4 |
|---|---|---|---|---|
| N-(2-hydroxy-3-stearoxypropyl)-N,N-dimethylamine | 2 | 2 | 2 | 2 |
| Dimethylaminopropyl-amide stearate | — | 2 | 2 | — |
| Stearyltrimethyl-ammonium chloride | 2 | 2 | 2 | 2 |
| Lauryltrimethyl-ammonium chloride | — | — | 0.5 | 0.5 |
| Cetanol | q.s. | q.s. | q.s. | q.s. |

TABLE 1-continued

|  |  |  |  |  |
|---|---|---|---|---|
| 2-amino-2-methyl-1-propanol | q.s. | q.s. | q.s. | q.s. |
| Purified water | balance | balance | balance | balance |
| pH | 8.11 | 8.64 | 8.96 | 8.56 |

|  | Example 5 | Example 6 | Comparative Example 1 | Comparative Example 2 |
|---|---|---|---|---|
| N-(2-hydroxy-3-stearoxypropyl)-N,N-dimethylamine | 2 | 2 | — | 2 |
| Dimethylaminopropylamide stearate | 3 | 2 | — | 2 |
| Stearyltrimethyl-ammonium chloride | 2 | 4 | 2 | — |
| Lauryltrimethyl-ammonium chloride | 0.5 | 0.5 | 0.5 | — |
| Cetanol | q.s. | q.s. | q.s. | q.s. |
| 2-amino-2-methyl-1-propanol | q.s. | q.s. | q.s. | q.s. |
| Purified water | balance | balance | balance | balance |
| pH | 9.01 | 9.06 | 3.64 | 8.52 |

(1) Measurement of Flexibility (Softness)

A hair bundle consisting of 200 hair strands was used, and the bundle was dipped into water. The bundle was placed in a testing machine (manufactured by Kato Tech Co., Ltd.) to measure a flexural stress for 3 times. Subsequently, the bundle was dipped into water again, and a flexural stress was measured for 3 times in the same manner. An average value of the 6 measurement values was used as a flexural stress before treatment.

Next, 0.5 g of each of the compositions was applied on the bundle, and a flexural stress after rinsing was measured for 6 times in the same manner as in the measurement before the application to obtain an average value of the measurements as a flexural stress after treatment.

For each of the compositions, a flexural stress variation was obtained by subtracting the flexural stress before treatment from the flexural stress after treatment. The values of the flexural stress variations of the compositions are shown as a graph in FIG. 1.

Examples 7 to 11 and Comparative Examples 3 to 5

Hair treatment compositions containing the components listed in Table 2 shown below were prepared.

Production process: Each of the compositions was obtained by adding other components to hot water of 80° C., dissolving by stirring, and cooling to 40° C. Changes in flexibility (softness) and smoothness of the hair before and after application of each of the compositions were measured.

TABLE 2

|  | Comparative Example 3 | Example 7 | Example 8 | Example 9 |
|---|---|---|---|---|
| N-(2-hydroxy-3-stearoxypropyl)-N,N-dimethylamine | 2 | 2 | 2 | 2 |
| Dimethylaminopropylamide stearate | 2 | 2 | 2 | — |
| Stearyltrimethyl-ammonium chloride | — | 2 | — | 2 |
| Lauryltrimethyl-ammonium chloride | — | — | 0.5 | — |
| Behenyltrimethyl-ammonium chloride | — | — | — | 2 |
| Cetanol | q.s. | q.s. | q.s. | q.s. |
| 2-amino-2-methyl-1-propanol | q.s. | q.s. | q.s. | q.s. |
| Propylene glycol | 8 | 8 | 8 | 8 |
| Sorbitol | 4 | 4 | 4 | 4 |
| Purified water | balance | balance | balance | balance |
| pH | 8.11 | 8.64 | 8.96 | 8.56 |

|  | Example 10 | Example 11 | Comparative Example 4 | Comparative Example 5 |
|---|---|---|---|---|
| N-(2-hydroxy-3-stearoxypropyl)-N,N-dimethylamine | 2 | 2 | — | — |
| Dimethylaminopropylamide stearate | 2 | 2 | — | — |
| Stearyltrimethyl-ammonium chloride | 2 | — | 2 | — |
| Lauryltrimethyl-ammonium chloride | 0.5 | 0.5 | 0.5 | 0.5 |
| Behenyltrimethyl-ammonium chloride | — | 2 | — | 2 |
| Cetanol | q.s. | q.s. | q.s. | q.s. |
| 2-amino-2-methyl-1-propanol | q.s. | q.s. | q.s. | q.s. |
| Purified water | balance | balance | balance | balance |
| pH | 9.01 | 9.06 | 9.06 | 9.06 |

(2) Measurement of Smoothness

A pulley method was employed for a measurement of smoothness. More specifically, a strand of hair was suspended on a pulley, and weights having an identical weight (W) were attached to both ends of the hair. One (T1) of the weights was placed on a scale of a scale balance, and the other (T2) was suspended. The pulley was balanced by rotating in a T1 direction, and a dynamic friction coefficient μk of the hair was calculated by using the following expression from a load (W) on T1 and a load (W—F) on T2 (provided that F is a reaction force from the scale balance, i.e. read of the scale balance):

$$\mu k = (1/\pi)\ln(T1/T2).$$

The dynamic friction coefficient of the hair before and after a treatment with each of the compositions listed in Table 1, which was calculated from the expression, was measured. Results are shown in FIG. 2.

From the results shown in FIGS. 1 and 2, the change in flexural stresses before and after treatment of the composition (Comparative Example 2) consisting of only the tertiary amine is very small to reveal an inferior effect of imparting flexibility to the hair. Also, the smoothness of the hair was unsatisfactory (Comparative Example 3). On the other hand, the composition consisting of only the quaternary ammonium salt shows the effect of imparting flexibility (Comparative Example 1), but it is impossible to impart satisfactory smoothness by the combination of the quaternary ammonium salts (Comparative Examples 4 and 5). In contrast, in the case of the treatment with the compositions (Examples 1 to 11) of the present invention, flexibility and smoothness are imparted to the hair.

Example 12 and Comparative Example 6

Hair treatment compositions containing the components listed in Table 3 shown below were prepared.

Production process: Each of the compositions was obtained by adding other components to hot water of 80° C., dissolving by stirring, and cooling to 40° C. A chemical treatment (treatment with a commercially available two-package oxidation hair dye product) was performed on a hair on which the composition was applied, and changes in smoothness and flexibility of the hair after the chemical treatment were measured.

TABLE 3

|  | Comparative Example 6 | Example 12 |
| --- | --- | --- |
| Stearoxytrimethylammonium bromide | 4 | — |
| N-(2-hydroxy-3-stearoxypropyl)-N,N-dimethylamine | — | 2 |
| Lauryltrimethylammonium chloride | — | 0.6 |
| Dimethylaminopropylamide stearate | — | 2.2 |
| Stearyl alcohol | 7 | 0.8 |
| Sorbitol | 1 | 5 |
| 1,3-butylene glycol | 3 | 10 |
| Cyclomethicone | 2 | — |
| Dimethicone | 3 | 10 |
| Polyoxyethylene alkyl ether | 7 | 4 |
| 2-amino-2-methyl-1-propanol | — | 0.1 |
| Lactic acid | 0.4 | — |
| Purified water | balance | balance |
| pH | 4.6 | 7.8 |

The smoothness of the hair was evaluated by applying 1.5 g of each of the compositions on a hair bundle, dyeing by applying the commercially available two-package oxidation hair dye product at 30° C. for 29 minutes on the hair bundle on the composition, rinsing, and measuring a force (load) required for combing the bundle. Results are shown in FIG. 3.

The flexibility was evaluated by using a value of flexural stress variation described above. Results are shown in FIG. 4.

From the results shown in FIG. 3, in the case of treating with Comparative Example 6 which is the conventional treatment agent (containing a cationic surfactant but not containing the tertiary amine), the smoothness was better than that of the hair without pretreatment in a wet state (FIG. 3, WET), but the smoothness attained in a dry state was equal or inferior to the hair without pretreatment (FIG. 3, DRY). In contrast, the hair pretreated with the composition (Example 12) of the present invention showed the smoothness which is equal to that of the conventional treatment agent (Comparative Example 6) in a wet state, and the smoothness in a dry state was very much improved as compared to the no treatment case and the treatment with the conventional treatment agent.

From the results shown in FIG. 4, it is confirmed that the hair treated with the composition (Example 12) of the present invention has the flexibility which is equal to the conventional treatment agent (Comparative Example 6) in the dry state and attains the further improved flexibility in the wet state.

Formulation Example 1

| Hair treatment composition | |
| --- | --- |
| Components | Amount (% by mass) |
| Dimethylaminopropylamide stearate | 2.0 |
| Stearyltrimethylammonium chloride | 2.0 |
| Stearyl alcohol | 1.0 |
| Sorbitol | 10.0 |
| 1,3-butylene glycol | 10.0 |
| L-glutamic acid | 0.1 |
| Hydrolyzed wheat protein | 0.1 |
| Phenoxy ethanol | 0.3 |
| Aromatic agent | 0.2 |
| Water | Balance |

Production Method:

The hair treatment composition was obtained by heating water, adding other components, dissolving by stirring, performing an emulsifying processing by using a homomixer, and cooling.

Formulation Example 2

| Hair treatment composition | |
| --- | --- |
| Components | Amount (% by mass) |
| N-(2-hydroxy-3-stearoxypropyl)-N,N-dimethylamine | 4.0 |
| Lauryltrimethylammonium chloride | 0.3 |
| Cetanol | 0.6 |
| Dipropylene glycol | 13.0 |
| Citric acid | 0.1 |
| Highly polymerized dimethylpolysiloxane-methyl (aminopropyl)siloxane copolymer emulsion | 10.0 |
| Phenoxy ethanol | 0.4 |
| Aromatic agent | 0.3 |
| Water | Balance |

Production Method:

The hair treatment composition was obtained by heating water, adding other components, dissolving by stirring, performing an emulsifying processing by using a homomixer, and cooling.

Formulation Example 3

| Hair treatment composition | |
| --- | --- |
| Components | Amount (% by mass) |
| N-(2-hydroxy-3-stearoxypropyl)-N,N-dimethylamine | 1.5 |
| Diethylaminoethylamide stearate | 2.3 |
| Stearyltrimethylammonium chloride | 2.0 |
| Behenyl alcohol | 1.0 |
| Propylene glycol | 10.0 |
| Glycerin | 10.0 |
| Highly polymerized methylpolysiloxane | 5.0 |

-continued

Hair treatment composition

| Components | Amount (% by mass) |
|---|---|
| O-[2-hydroxy-3-(trimethylammonio)propyl]-hydroxyethylcellulose chloride | 0.8 |
| Highly polymerized polyethylene glycol | 0.03 |
| Phenoxy ethanol | 0.5 |
| Aromatic agent | 0.3 |
| Water | Balance |

Production Method:

The hair treatment composition was obtained by heating water, adding other components, dissolving by stirring, performing an emulsifying processing by using a homomixer, and cooling.

INDUSTRIAL APPLICABILITY

The hair treatment composition of the present invention is capable of imparting flexibility and smoothness to the hair after a chemical treatment when used before or simultaneously with the chemical treatment such as permanent wave formation and dyeing, thereby making it possible to omit a post-treatment such as the conventional hair treatment. Also, since the hair treatment composition of the present invention is a single-package composition, it has an excellent usability and is particularly suitable for use in hair salons and the like.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. A hair treatment composition comprising:

(A) a tertiary amine represented by the following formula (I):

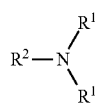

(I)

(wherein $R^1$ may be the same or different and each represents a $C_{1-3}$ alkyl group or benzyl group which may optionally be substituted by a hydroxyl group; and $R^2$ represents a $C_{8-36}$ straight chain or branched chain alkyl group which may optionally be substituted by a hydroxyl group or a $R^3$-(Y)—(Z)-group, in which $R^3$ is a $C_{8-36}$ straight chain or branched chain alkyl group which may optionally be substituted by a hydroxyl group; Y is a linking group selected from an amide linkage (—CONH—), an ether linkage (—O—), and an ester linkage (—COO—); and Z is a linking group selected from —CH$_2$CH$_2$CH$_2$— and —CH$_2$CH(OH)CH$_2$—);

(B) a quaternary ammonium salt represented by the following formula (II):

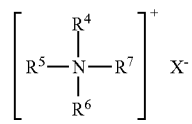

(II)

(wherein $R^4$, $R^5$, $R^6$, and $R^7$ may be the same or different with at least one of $R^4$, $R^5$, $R^6$, and $R^7$ representing a $C_{3-36}$ straight chain or branched chain alkyl group or alkenyl group while each of the rest representing a $C_{1-3}$ alkyl group or benzyl group which may optionally be substituted by a hydroxyl group; and $X^-$ represents an anion); and (C) a higher alcohol, characterized in that a ratio ((C)/[(A)+(B)]) of an amount of (C) higher alcohol to a total amount ([(A)+(B)]) of (A) tertiary amine and the (B) quaternary ammonium salt is within a range of 0.1 to 1.0 ; and that the composition as a whole has a pH of 7.0 or more.

2. The hair treatment composition according to claim 1, characterized in that:

an amount of (A) tertiary amine is 0.01 to 10% by mass;

an amount of (B) quaternary ammonium salt is 0.01 to 10% by mass; and an amount of (C) higher alcohol is 0.01 to 10% by mass.

3. The hair treatment composition according to claim 1, characterized in that:

(A) tertiary amine is one or a mixture of two selected from N-(2-hydroxy-3-stearoxypropyl)-N,N-dimethylamine and dimethylaminopropylamide stearate.

4. The hair treatment composition according to claim 1, characterized in that (B) quaternary ammonium salt is one or a mixture of two selected from lauryltrimethylammonium chloride and stearyltrimethylammonium chloride.

5. The hair treatment composition according to claim 1, characterized in that:

(C) higher alcohol is one or a mixture of two or more selected from stearyl alcohol, behenyl alcohol, oleyl alcohol, and cetostearyl alcohol.

6. The hair treatment composition according to claim 2, characterized in that:

(A) tertiary amine is one or a mixture of two selected from N-(2-hydroxy-3-stearoxypropyl)-N,N-dimethylamine and dimethylaminopropylamide stearate.

7. The hair treatment composition according to claim 2, characterized in that:

(B) quaternary ammonium salt is one or a mixture of two selected from lauryltrimethylammonium chloride and stearyltrimethylammonium chloride.

8. The hair treatment composition according to claim 3, characterized in that:

(B) quaternary ammonium salt is one or a mixture of two selected from lauryltrimethylammonium chloride and stearyltrimethylammonium chloride.

9. The hair treatment composition according to claim 2, characterized in that:
(C) higher alcohol is one or a mixture of two or more selected from stearyl alcohol, behenyl alcohol, oleyl alcohol, and cetostearyl alcohol.

10. The hair treatment composition according to claim 3, characterized in that:
(C) higher alcohol is one or a mixture of two or more selected from stearyl alcohol, behenyl alcohol, oleyl alcohol, and cetostearyl alcohol.

11. The hair treatment composition according to claim 4, characterized in that:
(C) higher alcohol is one or a mixture of two or more selected from stearyl alcohol, behenyl alcohol, oleyl alcohol, and cetostearyl alcohol.

* * * * *